(12) United States Patent
Klein (10) Patent No.: US 7,460,226 B2
(45) Date of Patent: Dec. 2, 2008

(54) SPECTROPHOTOMETER

(75) Inventor: Cornelis Kees Klein, Hamilton (NZ)

(73) Assignee: Klein Medical Limited, Devonport, Auckland (NZ)

( * ) Notice: Subject to any disclaimer, the term of this patent is extended or adjusted under 35 U.S.C. 154(b) by 0 days.

(21) Appl. No.: 10/527,730

(22) PCT Filed: Sep. 15, 2003

(86) PCT No.: PCT/NZ03/00207

§ 371 (c)(1), (2), (4) Date: Oct. 20, 2005

(87) PCT Pub. No.: WO2004/025233

PCT Pub. Date: Mar. 25, 2004

(65) Prior Publication Data

US 2006/0146324 A1 Jul. 6, 2006

(30) Foreign Application Priority Data

Sep. 13, 2002 (NZ) .................................... 521406
Sep. 13, 2002 (NZ) .................................... 521407

(51) Int. Cl.
*G01J 3/30* (2006.01)
(52) U.S. Cl. ...................... 356/317; 356/326; 250/493.1
(58) Field of Classification Search ................. 356/302, 356/317, 326; 250/493.1
See application file for complete search history.

(56) References Cited

U.S. PATENT DOCUMENTS

| 3,955,082 A * | 5/1976 | Dyment ...................... 257/184 |
| 4,158,505 A * | 6/1979 | Mathisen et al. ............. 356/308 |
| 4,832,491 A | 5/1989 | Sharpe et al. |
| 5,357,343 A | 10/1994 | Lowne et al. |
| 5,602,647 A | 2/1997 | Xu et al. |
| 5,652,654 A | 7/1997 | Asimopoulos |
| 5,684,582 A | 11/1997 | Eastman et al. |
| 5,737,076 A | 4/1998 | Glaus et al. |
| 5,818,048 A | 10/1998 | Sodickson et al. |
| 7,154,599 B2 * | 12/2006 | Adams et al. ................ 356/317 |

FOREIGN PATENT DOCUMENTS

| EP | 0 192 200 A2 | 8/1986 |
| GB | 2 049 165 A | 12/1980 |
| GB | 2049165 A | 12/1980 |
| WO | WO 96/31764 A1 | 10/1996 |
| WO | WO 00/33039 A | 6/2000 |

* cited by examiner

*Primary Examiner*—Kara E. Geisel
*Assistant Examiner*—Abdullahi Nur
(74) *Attorney, Agent, or Firm*—Townsend and Townsend and Crew, LLP (57) ABSTRACT

An analyzer or spectrophotometer for the detection of material is described with a single source with variable intensity, a single detector having a variable spectral response where the sample is able to be analyzed based on varying the intensity and spectral response. Various methods are described for varying the intensity, and also for varying the spectral response.

33 Claims, 12 Drawing Sheets

Figure 7

SPECTROPHOTOMETER

FIELD OF INVENTION

The present invention relates to a system for analysing the spectral absorption of a material in a test sample, and in particular to improvements in the system of the type using detection apparatus.

BACKGROUND OF THE INVENTION

The simplest spectroscope splits incident visible light into spectral lines that can be observed by the human eye. In more complicated analysis, for example spectrochemical analysis, the substance under investigation is heated, so that it emits radiation. Each component of the substance emits a characteristic radiation, and this can be used as a means of identification. The radiation is passed through a diffraction grating or a prism to separate it into its constituent wavelengths. Detectors are then used to observe or record details of the spectrum, and instrument can be used to measure the wavelengths and intensities of spectral lines. A permanent record of the results (a spectrograph) may be made to allow more detailed analysis. Comparison of the spectrum with the spectra of known, pure, substances allows the components to be identified and, with quantitative analysis, their relative proportions determined. This offers an extremely sensitive method of analysis of chemical substances, and automated spectroscopic procedures are now used routinely in laboratories.

Most laboratory apparatus are currently used for the measurement of the concentration of a material in a solution are relatively complex in nature. Their degree of complexity is at least partially a cause for several disadvantages firstly they are relatively expensive. Secondly they are often relatively delicate as they use prisms and dispersion gratings and are generally unsuitable for use in the field or in normal manufacturing and processing environments. And thirdly they are generally specific in purpose and often cannot be readily adapted for other applications.

The term 'material' shall be used in its broadest sense and shall not be restricted to solid matter but also to liquids or gases. In addition the term 'solution' shall also be taken to include the gaseous phase.

International patent application number WO96/31764 discloses a method and apparatus for the quantitative determination of particles in fluid. This apparatus comprises one or more light emitters, and one or more light detectors sensitive to the output of the emitters. Data is gathered from a plurality of signal paths between the emitter and detector. This data is subsequently evaluated by comparison with known data for different fluid particles in a fluid sample.

U.S. Pat. No. 4,158,505 describes a spectrophotometer consisting of a wideband light source, paths provided for the sample and reference lights, a chopper wheel allowing the sample and reference light to be interspersed with dark period, and be alternately incident on a dispersion grating and thus transmitted onto a linear array of photodiodes.

U.S. Pat. No. 3,955,082 describes a single photodetector for measuring a variety of wavelengths. The single photodetector is constructed from a plurality of detector sections each having a variable bandwidth and controlled by varying the reverse bias voltage.

U.S. Pat. No. 5,357,343 describes a spectrophotometer consisting of a single emitter detector and rotating chopper. The rotary chopper contains filters to select wavelengths to be incident on the detector at anyone time. All the inventions described in each specification possess many of the general disadvantages described previously.

SUMMARY OF INVENTION

It is therefore an object of the present invention to provide a spectrophotometer which goes some way to overcoming the abovementioned disadvantages in the prior art or will at least provide the industry with a useful choice.

Accordingly in a first aspect the present invention consists in an analyser or spectrophotometer for the detection of material in a sample comprising:

a source adapted to direct radiation at least at said sample, the radiation incident on or reflected by said sample able to be varied;

a detector for detecting at least radiation reflected by said sample, wherein said detector having a spectral response able to be varied and an output depending on radiation incident thereon and said spectral response;

a controller or processor receiving said output, configured or programmed to vary the intensity of said source;

vary the spectral response of said detector; and determine a characteristic of said sample based on said output in relation to said variations.

In a second aspect the present invention consists in an analyser or spectrophotometer for the detection of material in a sample comprising:

means for directing radiation at said sample;

means for varying the radiation incident on or reflected by said sample;

means for detecting at least radiation reflected by said sample;

means for providing a variable spectral response output representative of said detected reflected radiation; and means for determining a characteristic of said sample based on said output in relation to said variations.

In a third aspect the present invention consists in a method of detecting material in a sample comprising the steps of directing radiation at said sample;

varying the radiation incident on or reflected by said sample;

detecting at least radiation reflected by said sample;

providing a variable spectral response output representative of said detected radiation; and determining a characteristic of said sample based on said output in relation to said variations.

Wherein the radiation directed at said sample is varied by varying the voltage or current supplied to the radiation source.

Wherein the radiation directed at said sample is varied by varying the transmission path between the radiation source and said sample.

Wherein the transmission path is varied by varying the size of the aperture through which radiation is directed at said sample.

Wherein the size of the aperture is varied by a rotating wheel with different sized apertures through which is directed at said sample.

Wherein the radiation directed at said sample is varied by the variation in intensity when switching the radiant source on or by pulsing the radiation source.

Wherein the radiation reflected by said sample is detected by a photodiode and the spectral response of said output is varied by varying the width of the depletion zone within said diode.

Wherein the width of the depletion zone within said diode is varied by varying the reverse voltage applied across the diode and the output being the resulting current.

Wherein said output signal from said detector is amplified and digitised prior to being supplied to said controller.

Wherein said controller is a microprocessor.

Wherein said detector is a photodiode detector.

Wherein said source is a light emitting diode.

Wherein said source is a tungsten filament lamp.

Wherein said source is a gas discharge lamp.

In a forth aspect the present invention consists in an an analyser or spectrophotometer for the detection of material in a sample comprising:

a source adapted to direct radiation at least at said sample;

a detector configured to provide an output indicative of at least radiation reflected by said sample;

a variable transmission path for radiation between said source, said sample or said detector;

a controller or processor receiving said output and operating said transmission path, configured or programmed to determine the radiation reflected from said source off said sample;

determine the radiation directly from said source; and determine a characteristic of said sample based on said output in relation to variations in said transmission path.

In a fifth aspect the present invention consists in an analyser or spectrophotometer for the detection of material in a sample comprising:

means for directing radiation at said sample;

means for detecting at least radiation reflected by said sample;

means for detecting at least radiation directly from said source; and means for determining a characteristic of said sample based on said reflected radiation in relation to said direct radiation.

In a sixth aspect the present invention consists in a method of detecting material in a sample comprising the steps of directing radiation at said sample;

detecting at least radiation reflected by said sample;

detecting at least radiation directly from said source; and determining a characteristic of said sample based on said reflected radiation in relation to said direct radiation.

Wherein said radiation reflects off said sample along a sample path and radiation passes directly to the detector along a reference path.

Wherein a blocking member having at least 3 cyclic modes a first mode during which said radiation passes said reference path, a second mode during which said radiation passes said sample path, and a third mode during which said radiation is blocked.

Wherein said blocking member is rotatable about a central axis.

Wherein during said first mode the intensity of said radiation through said sample path is varied.

Wherein the intensity is varied by providing different sized apertures in an annular path through said blocking member.

Wherein said blocking member includes indexing and a sensor(s) detect the position of said blocking member.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the foregoing and also envisages construction of which the following gives examples.

BRIEF DESCRIPTION OF THE DRAWINGS

Embodiment of the present invention will now be described with reference to the accompanying drawings in which.

DETAILED DESCRIPTION

One embodiment of the present invention relates to a spectrophotometer for providing a qualitative and quantitative measure of material size, density and spectral response of a sample. In particular, the spectrophotometer reads the reflectance of a sample. In an alternate embodiment, the spectrophotometer reads the absorbance of a sample. One embodiment of the apparatus of the present invention will comprise of at least one emitter and at least one detector. The emitter may be a single light emitter or alternately be comprised of an array of several light emitters that function as if a single light emitter. The detector may be a standard type photodiode capable of measuring a spectrum of frequencies commensurate with the application. The emitter and detector may be controlled by a microprocessor and/or in turn is connected to an external PC.

Figure 1:
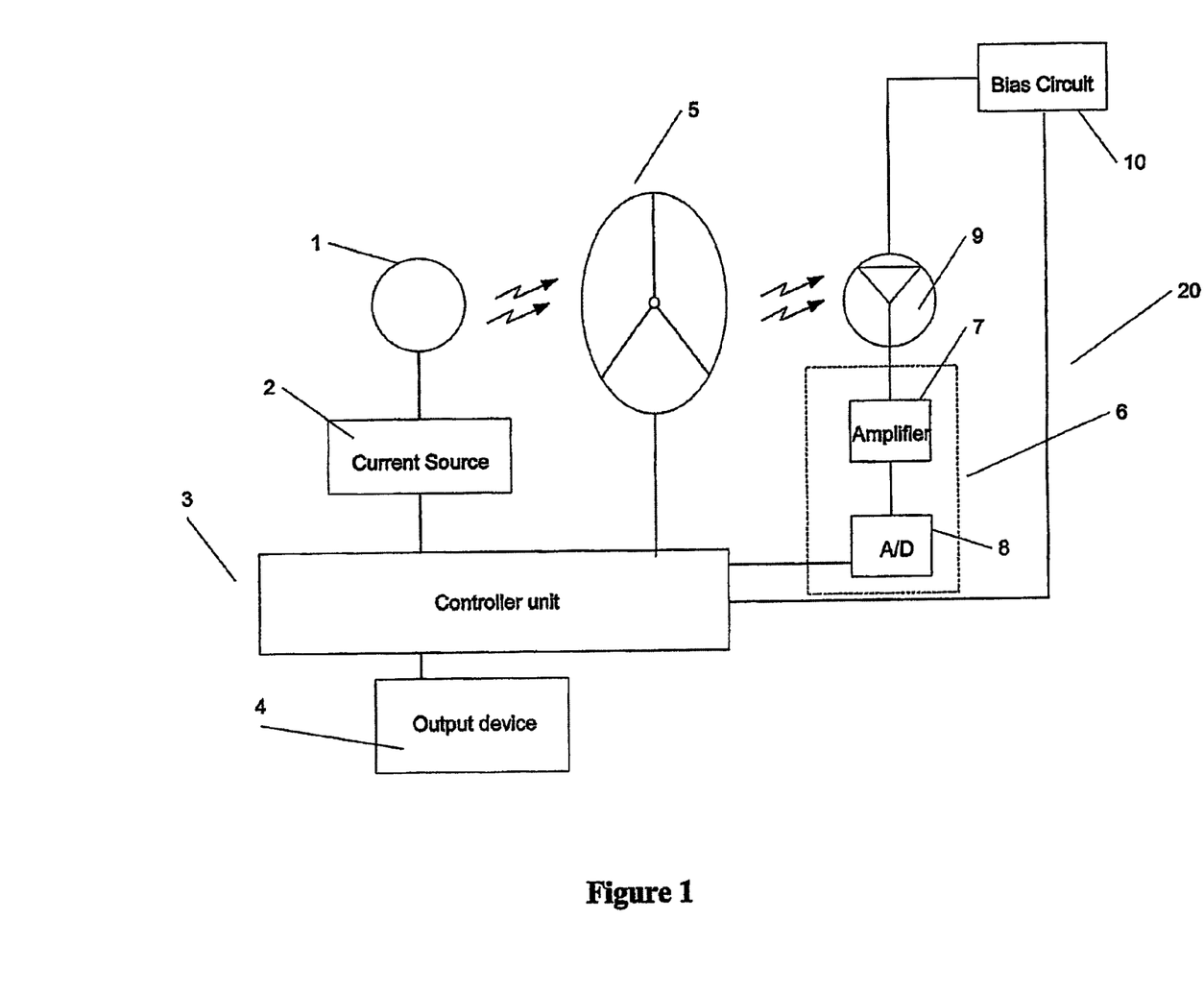
FIG. 1 shows a block diagram of the overall structure of the present invention.

Referring to FIG. 1 the light emitter 1 of the present invention generates radiation of a spectrum commensurate with the application. This may be over a broad range of frequencies including visible and infrared regions of the electromagnetic spectrum, a broadband signal, or a narrow band signal over a small range. Inexpensive emitters such as light emitting diodes, gas discharge lamps or tungsten filament lamps are examples. The detector 9 may for example be a photodiode to detect incident light signals.

The emitter 1 and detector 9 are both controlled by a controller module 3, for example a microprocessor. Microprocessor 3 includes software, control algorithms or component logic to achieve two things.

i) variation in the intensity of light reflected by the sample,
ii) variation of the spectral response of the detector.

Radiation Source

There are a number of ways of doing both but for simplicity only a few examples will be discussed here. For example the microprocessor 3 could control the intensity of the light emitted from the emitter 1 by varying the current supply 2. The operation of the detector 9 is controlled by varying the supply of voltage or reverse bias 10. Any signal generated by the detector 9 is amplified and converted into a digital format before being processed by the microprocessor 3.

Figure 2A:
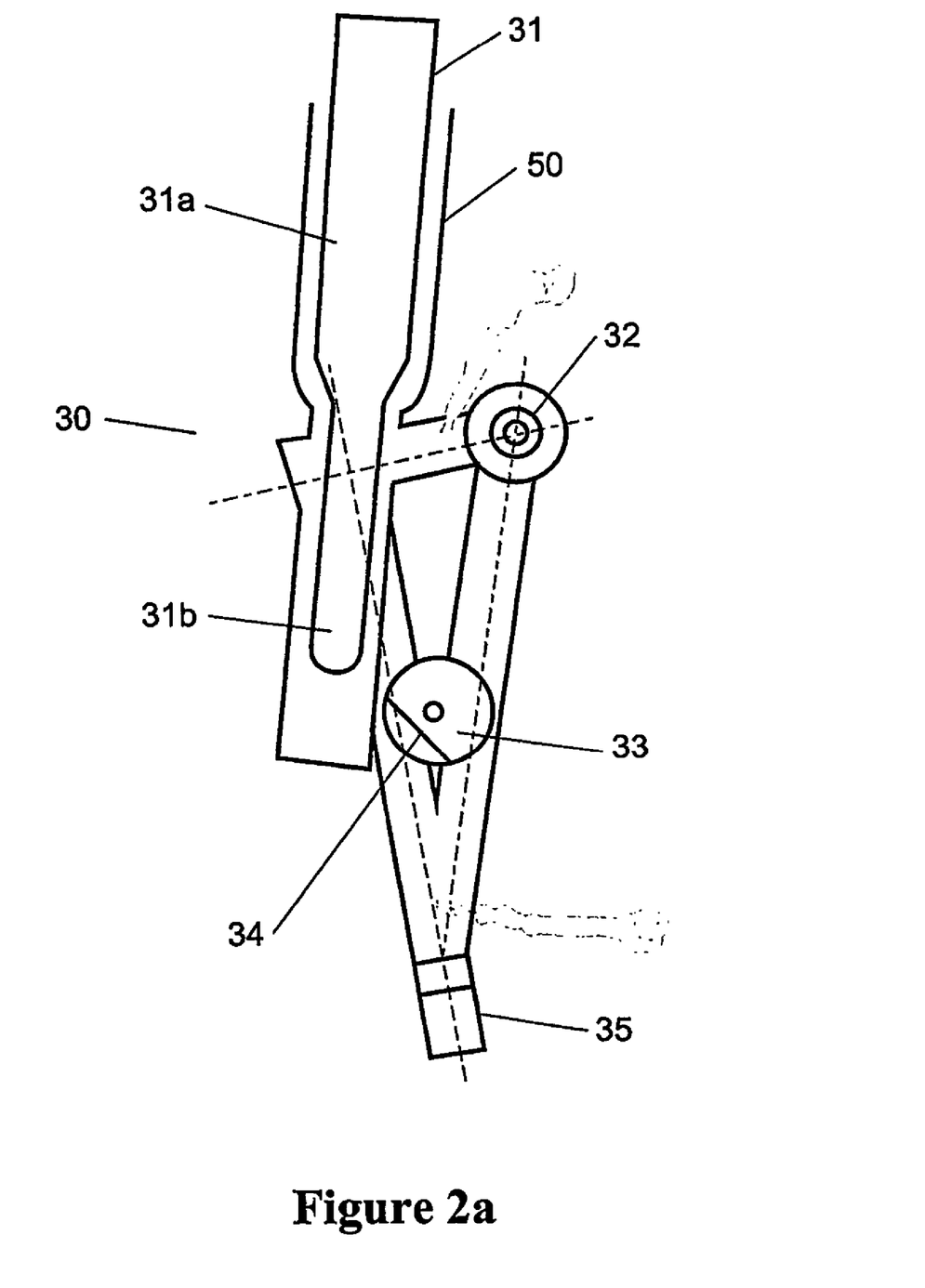
FIG. 2a shows a cross-sectional of the spectral analysing apparatus of the present invention.
Figure 2B:
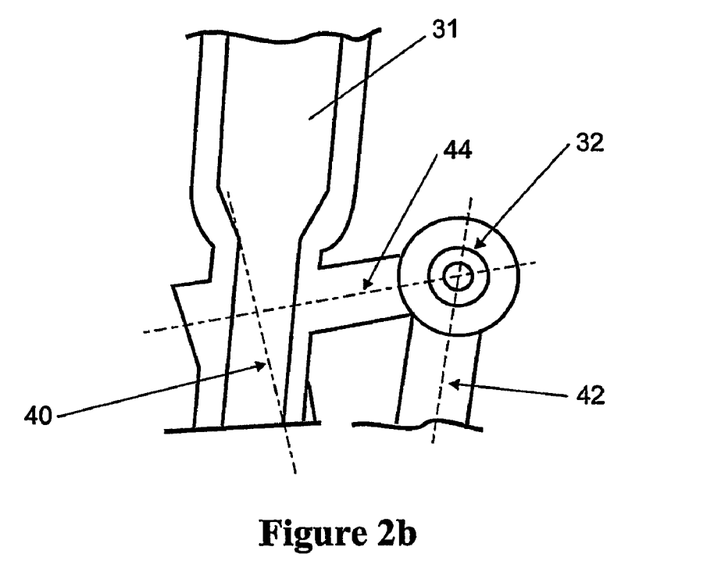
FIG. 2b shows a cross-sectional of the reflection angle through the sample being tested.
Figure 2C:
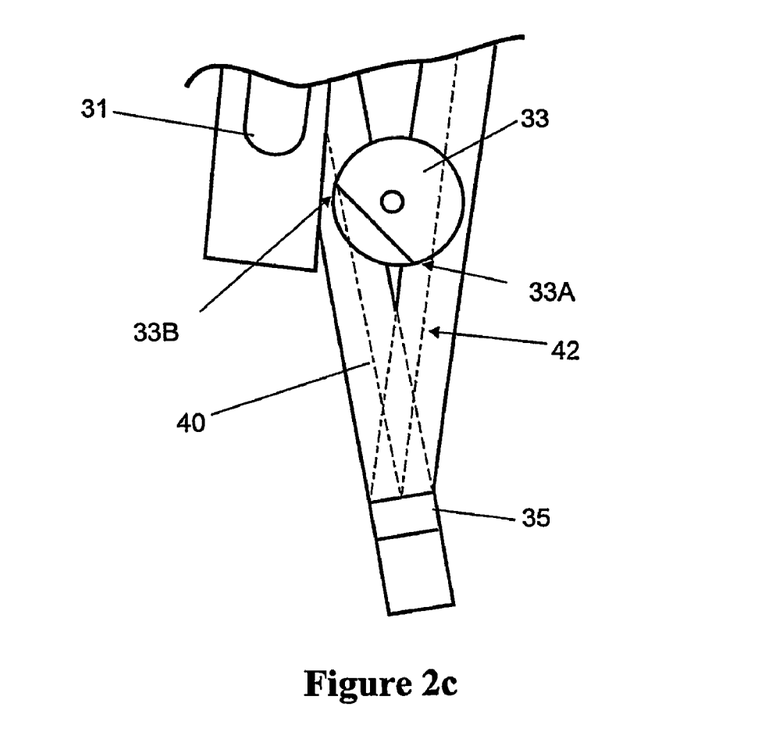
FIG. 2c shows a cross-sectional of the chopper wheel in the beam splitting apparatus.

In another embodiment, the light from the emitter 1 is split up into separate paths before falling incident on the detector 9 seen in FIG. 2c. This operation is performed by a device called a beam splitter or a chopping wheel 5. The rotation of the chopping wheel 5 may be controlled by the microprocessor 3 so that any one time, the detector 9 will only sense one signal. Typically the chopping wheel 5 blocks the path of other signals while allowing one signal to pass and fall incident on the detector 9. The three signals possible in this embodiment are the reference signal, sample signal and dark signal (no signal).

FIG. 2a illustrates the beam splitting apparatus 30 of the present invention. The beam splitting apparatus 30 is comprised of several elements, these include a light source 32, a chopping wheel 33, paths to direct the lights 40, 42 and 44, a detector 35, and a sample under test 31. The sample under test is typically contained by a test tube 31. The test tube 31 may be comprised of two diametrically different sections 31a and 31b. The lower section 31b of this test tube 31 has a smaller diameter than the top section 31a to allow for small amounts of a sample to be tested. Alternately a standard test tube may be used, this test tube has a regular diameter for its entire length. The test tube 31 containing the sample is inserted into a holding cavity 50 within the spectrophotometer for measurement.

FIG. 2b illustrates the reflection angle of the light from the light source 32 towards the chopper wheel 33, along path 44. The angle of reflection is substantially 90 degrees so that the reflected light, travelling along path 40, is perpendicular to the detector 35. This allows for optimum information transfer onto the light detector 35 with a minimum of diffraction distortion.

With reference to FIG. 2c, the chopper wheel is comprised of a circular type barrel with one section of the wheel being substantially flat 34. The depth of this flat section 34 is dictated by the diameter of the light transmission pathways 40, 42 and 44. The depth of the flat section 34 on wheel 33 may be substantially the same as the diameter of the light transmission pathway 42 and 44. Alternately, flat section 34 is approximately half way between the circular edge and the centre of rotation of the chopper wheel 33.

One complete revolution of the chopper wheel 33 will result in any one of three signals from the detector 35. These three signals include a reference signal, a sample signal, and a dark signal. The reference signal is when point 33a on the chopper wheel 33 is at substantially positive 10 degrees from the vertical axis. The information provided at the detector 35 is coming directly from the light source 32. The sample signal is detected when point 33b on the chopper wheel 33 is at substantially at negative 10 degrees from the vertical axis. This information at the detector 35 is comprised of the radiation coming from the reflectance off the sample. At any other time when there is no light incident on the detector 35 is known as the dark current. Dark current is important as it provides information for the calibration of the spectrophotometer. This information generally relates to the temperature drift of the detector 35 and the associated electronics.

Figure 3:
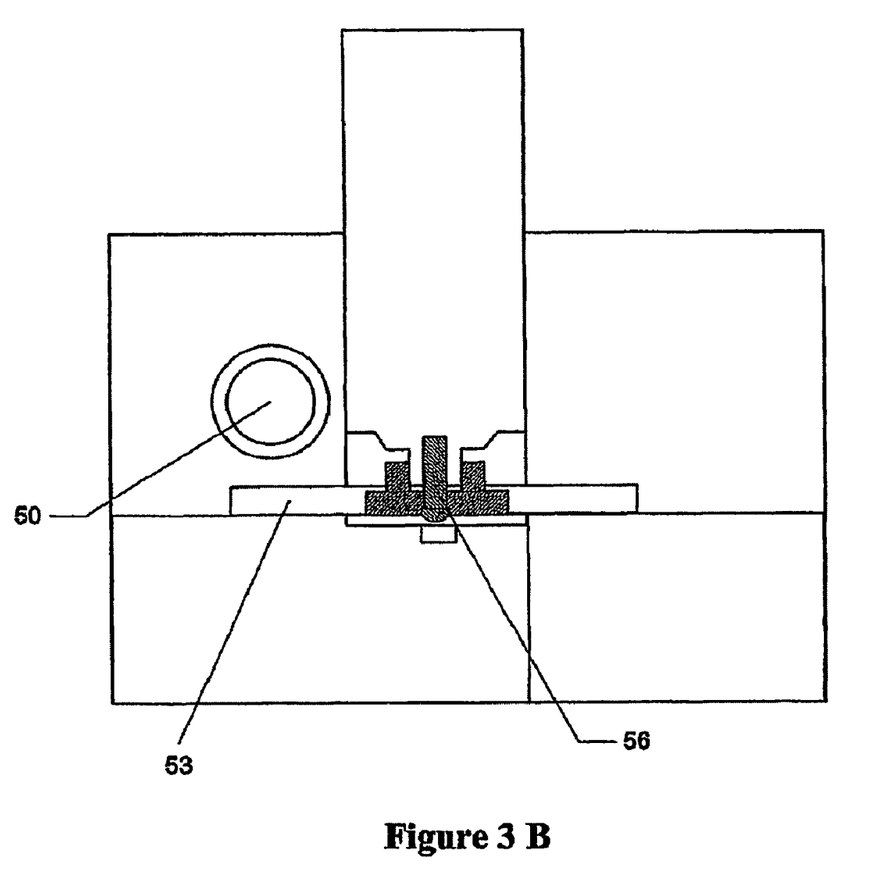
FIG. 3a shows a cross-sectional drawing of an alternate embodiment of the spectral analysing apparatus.
FIG. 3b shows a plan cross-sectional drawing of the alternate embodiment of the spectral analysing apparatus.
FIG. 3c is a section view of the chopping wheel of the alternate embodiment of the spectral analysing apparatus.
Figure 3A:
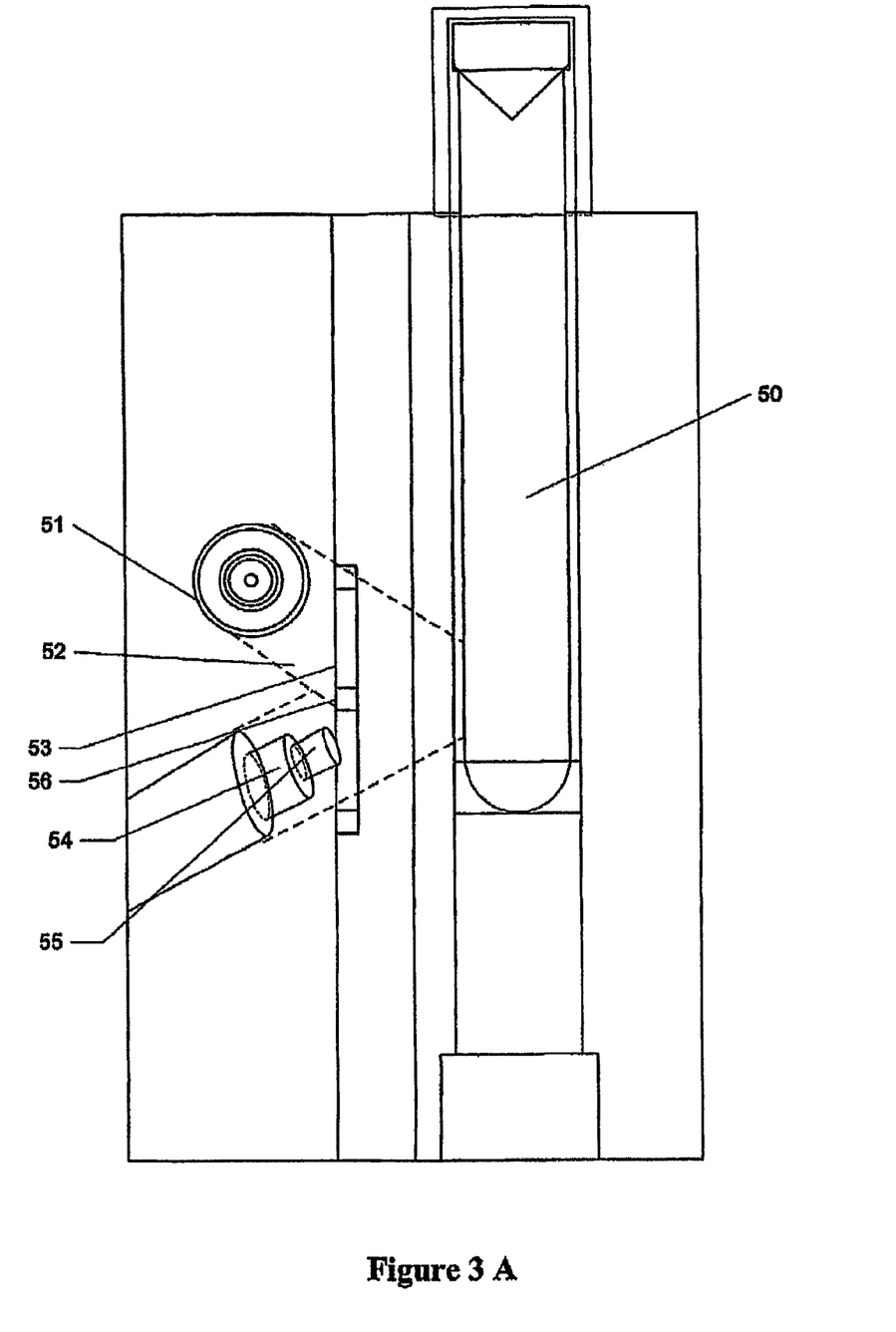
Figure 3C:
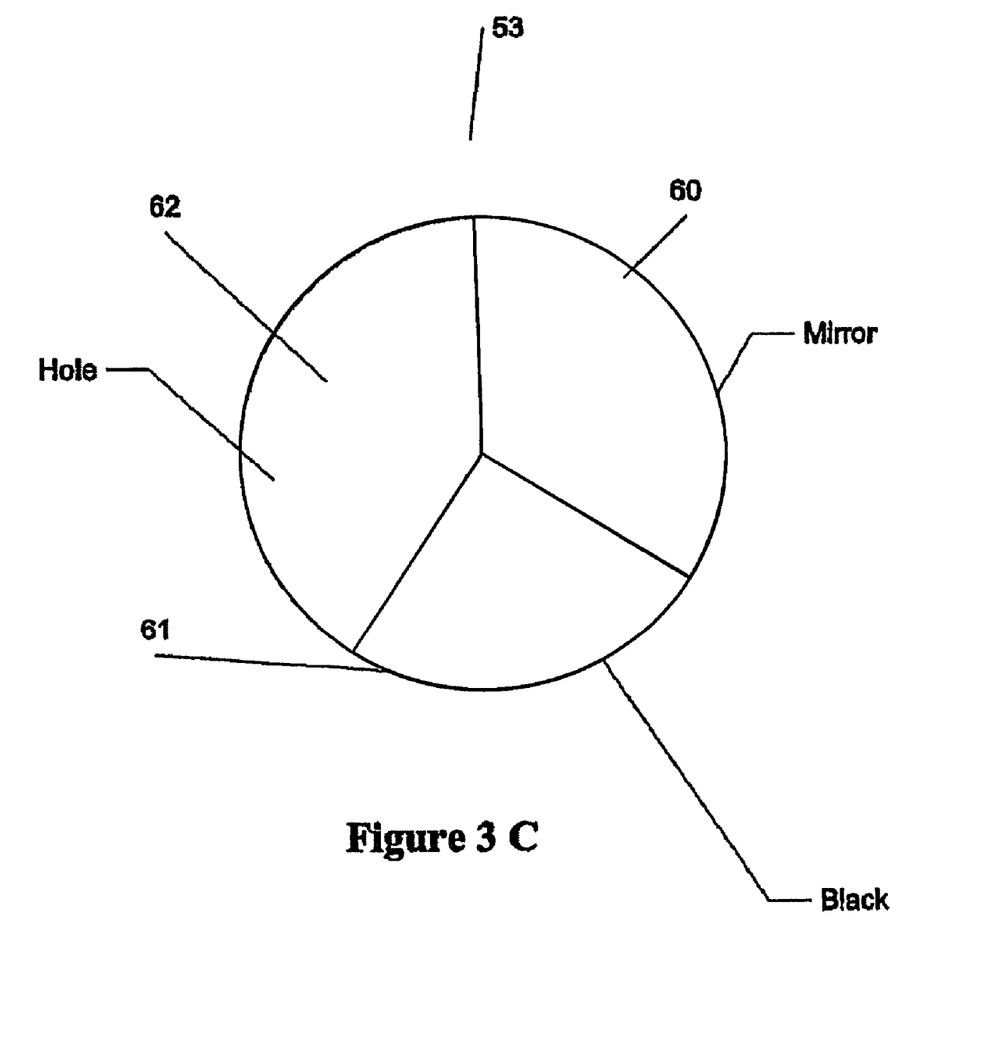

An alternative embodiment of the physical structure of the spectrophotometer is shown in FIGS. 3a to 3c. Referring to FIG. 3a, the angle between the light source 51 and detector 55 as it reflects off sample 50 is approximately 45°. The chopping wheel 56 dictates when the light signal will be incident on the detector 55. In FIG. 3c, the chopping wheel 53 is divided into three sections, namely a hole section 62, a mirror section 60 and a black section 61. The hole section 62 allows the signal to reflect off the sample 50 and be detected by the detector 55. The mirror section 60 reflects the signal directly to the detector 55. This results in reference readings. The black section 61 stops the transmission of light signal to the detector 55 so dark current readings may be taken. In this alternative embodiment, the chopping wheel 53 is off to one side of the sample 50. This allows transmission of the signal light through one section of the chopping wheel 53 at any one time, so simplifying the control of the chopping wheel 53.

Figure 6:
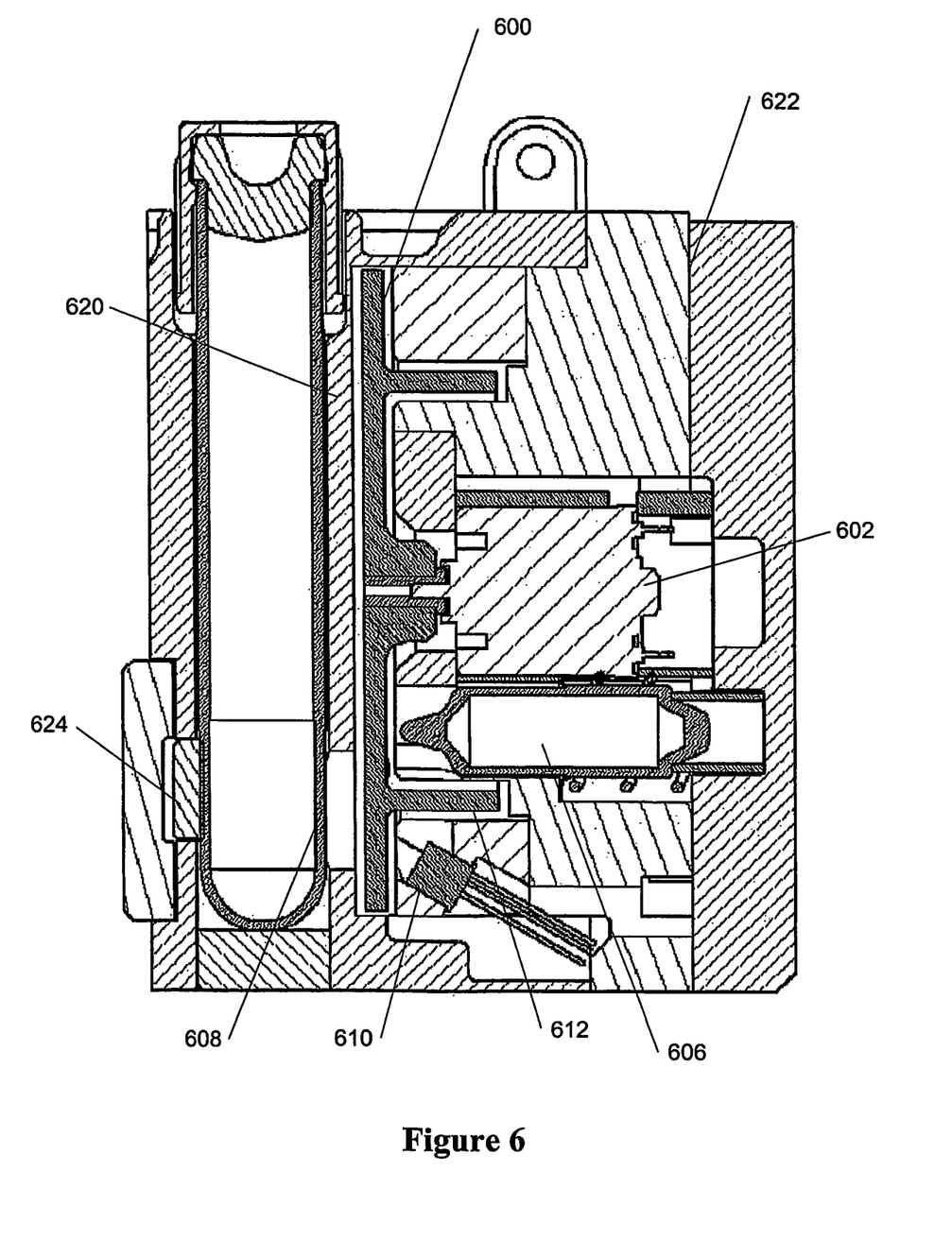
FIG. 6 is a section view through an alternative chopping wheel.
Figure 7:
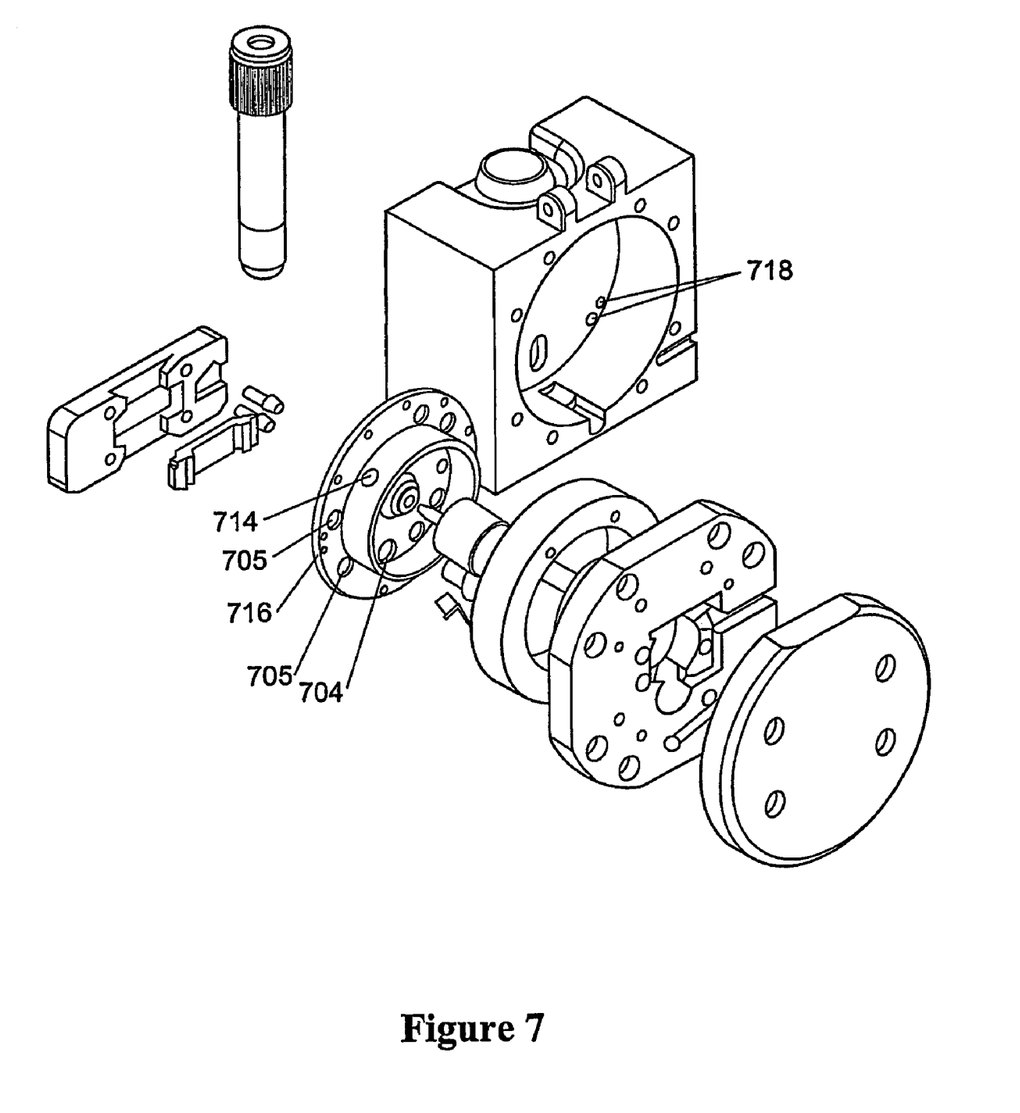
FIG. 7 is an exploded view of an alternative chopping wheel.

In a further improvement seen in FIGS. 6 and 7 the chopper wheel 600 may provide two functions, firstly varying the intensity of the light source reflected off the sample, as well as providing an intermittent direct path to the detector. This embodiment includes a wheel 600 driven by motor 602 with a number of apertures of varying diameter 704 which allow radiation from the source 606 to reflect off the sample 608 to the detector 610. These match up with apertures 705 in front of the detector 610 which don't vary in size. Wheel 600 also includes an axial rim 612 which blocks light directly from the source to the detector, except for a notch 714 to intermittently allow a direct path between the source and the detector and block the sample for calibration purposes. There are also a number of apertures around the periphery 716 and two sensors 718 in the base 620 to allow the microprocessor to calculate the position of the wheel such that the intensity of the light can be recorded alongside the signal received from the emitter. The moving parts are held into the base 620 by insert 622. Sample 608 is held in position by spring 624.

In a still further improvement variation of the intensity of the emitter could be achieved as the light source changes intensity over a very short period of time. For example when a filament is first turned on the amount of light emitted is not immediately at its maximum and takes a finite period of time to increase, which depends on the type of filament and the ambient temperature. In order to detect both the intensity of light generated and the consequent signal received by the detector different methods would need to be employed. For example intensity of the light generated could be detected by high resolution section of the voltage directly across the filament should give some indication of the change in intensity of the radiation generated. Alternatively the source could be pulsed.

Radiation Detector

Figure 4A:
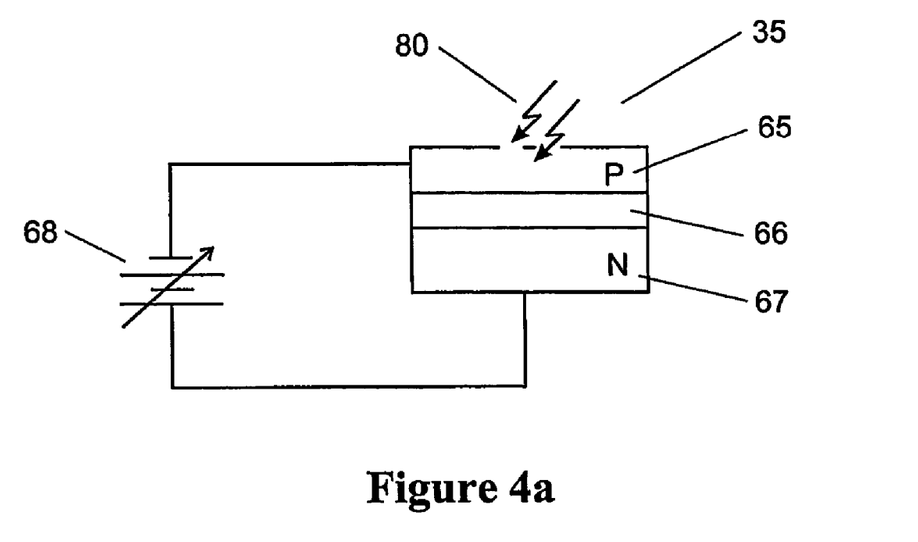
FIG. 4a illustrates how the photodetector is penetrated by short wavelength photons.
Figure 4B:
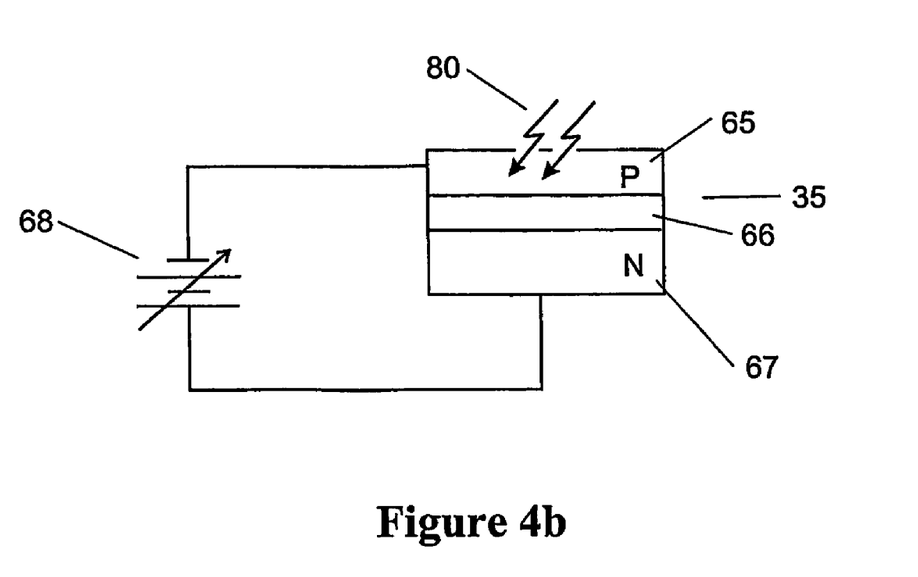
FIG. 4b illustrates how the photodetector is penetrated by long wavelength photons.

The detector 35 of the present invention is typically of a pn-junction or a p-i-n photodiode type. P-i-n junction photodiodes would provide the fast response necessary if high resolution encoding of incident radiation is required eg intensity changes as the source is turned on or pulsed. Referring to FIGS. 4a and 4b, the photodetector 35 is connected in reverse bias with a DC voltage source 68, in particular the negative terminal is connected to the p-side 65 of the diode 35 and the positive terminal is connected to the n-side 67 of the diode 35.

The operation of the detector 35 as it relates to the present invention will now be explained. When a photon of light is absorbed by the detector 35 it excites an electron and produces a single pair of charge carriers, an electron and a hole, where a hole is simply the absence of an electron in the diodes semiconductor lattice. Current passes through the semiconductor when the charge carriers separate and move in opposite directions. The detector 35 collects the photon-induced charge carriers that can be measured as current or voltage at its electrodes.

An n-type semiconductor material 67 may be doped with Silicon or Germanium to produce an excess of electrons, whereas a p-type material 65 has an excess of holes, or an electron deficiency. The area where these two materials meet is called the pn-junction. At the pn-junction, this disparity creates a concentration gradient that causes electrons to diffuse into the p-layer and holes to diffuse into the n-layer. This diffusion results in an opposing electrical potential, often referred to as an internal bias. Charge carriers cannot reside in this region, therefore it is termed the depletion region.

In detector 35 of the present invention, light enters the device through a thin p-type layer. Absorption causes light intensity to drop exponentially with penetration depth. Any photons absorbed near the depletion region produce charge carriers that are immediately separated and swept across the pn-junction by the inherent internal bias of the device. Charge carriers created outside the depletion region will move randomly, many of them eventually entering the depletion region to be swept rapidly across the pn-junction. Some of them will recombine and disappear without ever reaching the depletion region. This movement of charge carriers across the pn-junction upsets the electrical balance and produces a small photocurrent that is detected at the electrodes of the detector. The electrical current or voltage produced is proportional to the light intensity incident on the detector 35.

Figure 5A:
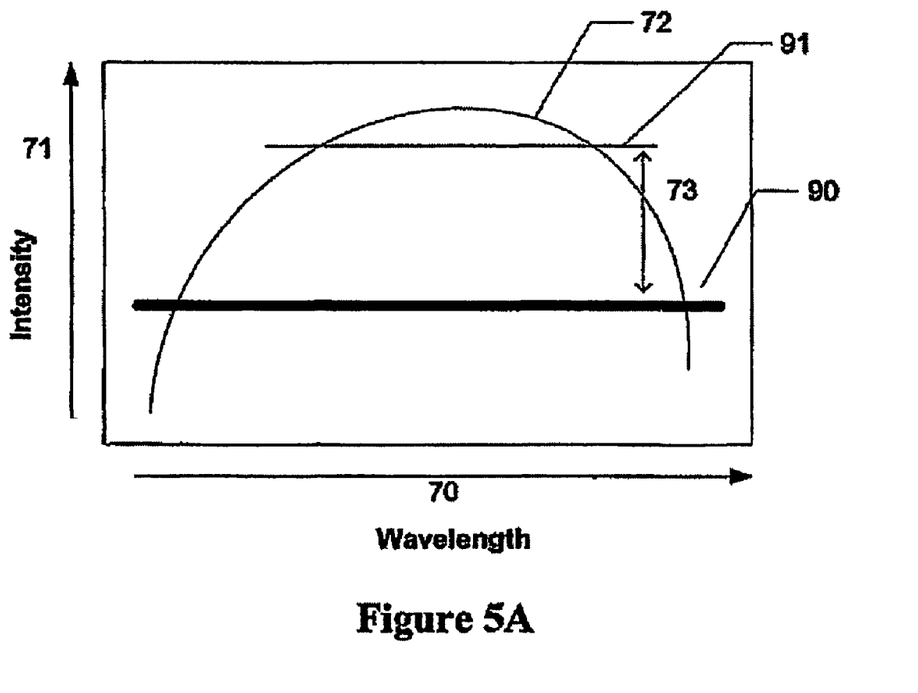
FIG. 5a shows the response of a typical photodetector by varying the intensity of the light source.

FIG. 5a, illustrates the response 72 of a typical detector 35 to a varying intensity 71 for a signal. It can be seen that varying the intensity 71 of the light source will affect the bandwidth or the total response 73 of the detector 35. In particular by increasing the intensity 71 of the light source to high level 91, the range of wavelengths 73 that can be measured at a particular time is decreased. Reducing the intensity 71 of the light source to low level 90 increases the range of wavelengths 73 that can be measured but only up to the maximum bandwidth response of the detector 72.

By increasing the intensity 71 of the light source 1, the Quantum efficiency of the detector is increased. The Quantum efficiency is defined as the ratio of the photocurrent in electrons to the incident light intensity in photons (or the sensitivity of the photodetectors to different wavelengths).

Referring to FIG. 4a, short wavelengths 80 of light penetrate a short distance into the structure of the detector 35 ie. light will interact close to the surface of the diode. Referring to FIG. 4b, longer wavelengths 81 of light penetrate deeper into the structure of the detector 35, or in extreme cases, the detector 35 becomes totally transparent to long wavelengths 81. Short wavelengths 80 of light are comprised of high energy photons while longer wavelengths 81 contain lower energy photons. The detector 35 only produces a current or voltage at its electrodes if the photons absorbed have enough energy or are close enough to traverse the pn-junction. This effect is called the 'cutoff wavelength'.

Photons with a wavelength less than the cutoff and in close proximity with the pn-junction will produce current or voltage. Photons with a longer wavelength greater than the cutoff will not produce current or voltage.

In order to control the cutoff wavelength it is desirable to control the thickness of the depletion region 66. One example way to expand this layer 66 is to apply an external electrical bias (voltage) 68. By applying an external electrical bias 68, the p-type 65 and n-type 67 regions reduce in thickness so reducing the efficiency of the longer wavelengths 81 in creating charge carriers. The thickness of these layers is directly controlled by the magnitude of external electrical bias 68. The greater the magnitude of external electrical bias 68, the thinner the region where charge carriers are formed 65 and 67 and the smaller the cutoff wavelength is. Ideally the control of the voltage 68 is provided by the microprocessor 3. One skilled in the art will appreciate other ways of varying the spectral response of the detector.

Figure 5B:
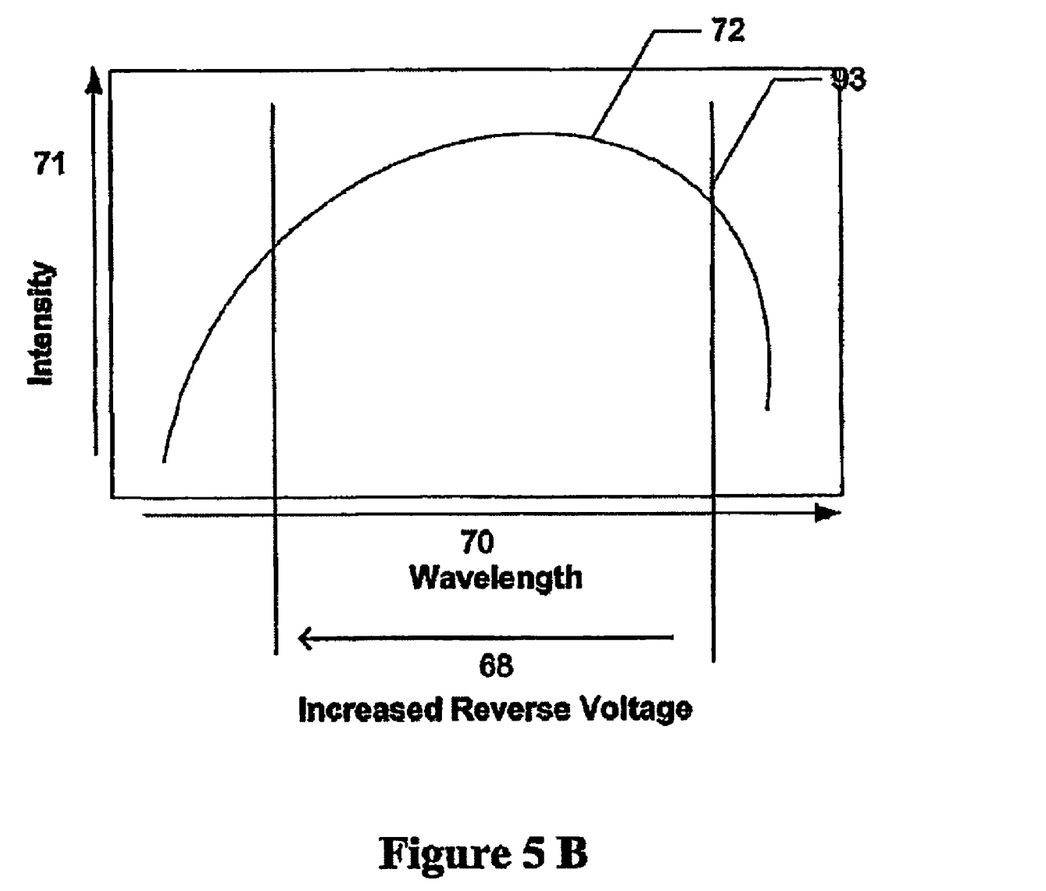
FIG. 5b shows the response of a typical photodetector by varying the reverse voltage across the photodetector.

FIG. 5b illustrates the incorporation of the external bias variable 68 to aid in the control of the detector 35. This external bias variable 68 is the magnitude of the external voltage 68 applied to the detector 35. As previously discussed, varying the voltage 68 varies the thickness of the region where charge carriers are formed 65 and 67 so effecting the response bandwidth of the detector 35. Specifically, by increasing the magnitude of the external voltage supply 68, the upper bandwidth response of the diode decreases 93. The control of external voltage 68 may be controlled by the microprocessor 3. Voltage 68 applied to the detector 35 may be changed in a stepwise manner. Alternately the external voltage 68 is changed in a continuous fashion.

Figure 5C:
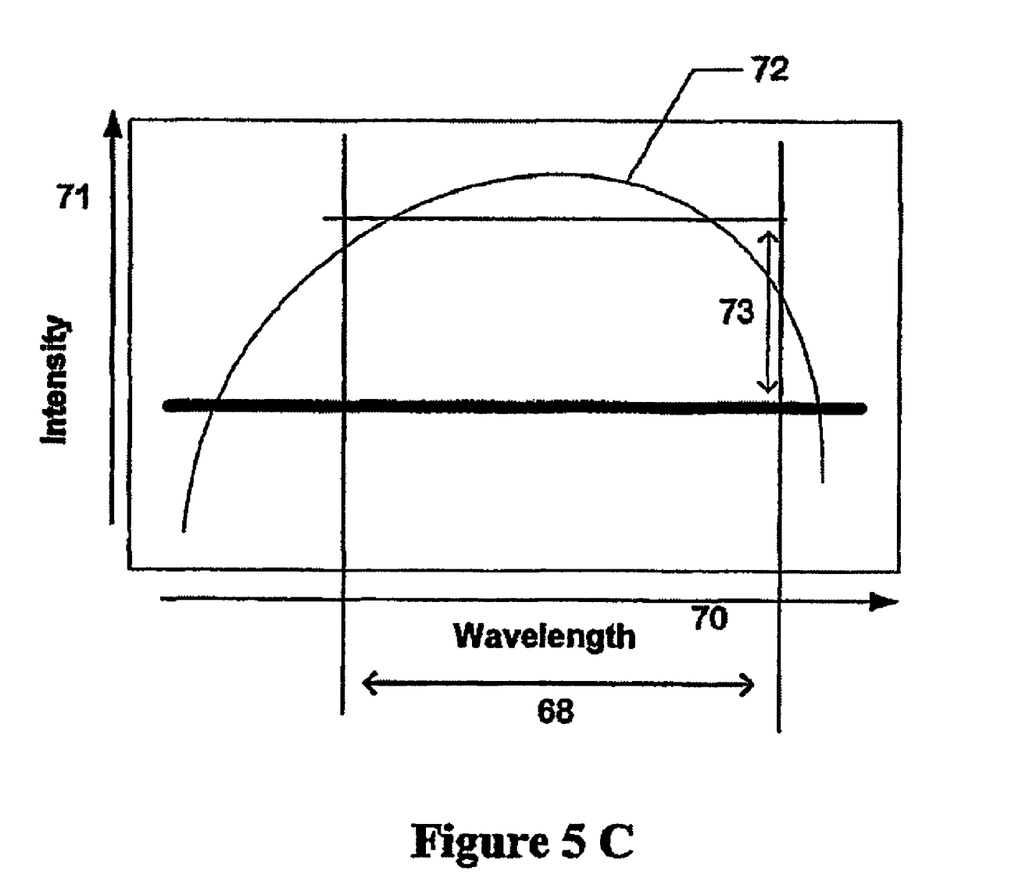
FIG. 5c shows the response of a typical photodetector by varying both the light intensity and the reverse voltage.

By combining the control of the light source intensity 71 and the external voltage applied 68 to the detector 35 by the microcontroller 3, individual components from the sample signal can be determined. In practise, for every stepped change in the external voltage 68, a number of different intensities 71 are emitted from the light source 1. For every cutoff band selected 70 a new range of detectable spectra is observed. The band sweep (due to bias voltage) and intensity sweep (due to light source) leads to a combined set of data points arranged across the full spectrum of the device under investigation. This way the characterisation of all the spectra under investigation is possible.

There are numerous possible embodiments in the process of analysing the spectral absorption of a material in a test sample. In one embodiment, a signal, for example the reference signal, is transmitted through the chopper wheel 33 to the detector 35. The controlling module, typically a microprocessor 3, selects a voltage to be supplied to the detector 35, controlling the width of the depletion region 66, and thus selects a predetermined bandwidth that the detector 35 will be sensitive to. The microprocessor 3 then varies the voltage supplied to the light source 1 thus varying the intensity of the broadband light signal. The detector 35 will send representative signals to the microprocessor 3. This data is then stored in the microprocessor until the test is finished. The changes in the level of voltage supplied to the detector 35, selects detection bandwidths. This process repeats until measurements have been performed at all preselected bandwidths. The entire process is repeated again for the next light signal, for example the light signal from the sample path.

In another embodiment of the present invention, one signal, for example the reference signal, is transmitted through the chopping wheel to the detector. The microprocessor selects the predetermined bandwidth that the detector is sensitive to, performed by selecting the voltage level supplied to the detector. The microprocessor 3 then varies the voltage level supplied to the light source thus varying the intensity of the light signal. The detector generates representative signals that are transmitted to the microprocessor. The chopper wheel then rotates and blocks the reference signal and allows the next signal to be transmitted, for example the sample signal. Again the microprocessor varies the intensity of the light source and the measured values are stored in the microprocessor. As the chopper wheel rotates again there is a dark interval, this is known as the dark current. There is no light incident on the detector but an inherent current will flow across the pn-junction of the photodiode. This current level is measured and used by the microprocessor to calibrate for any temperature drift in the electronics.

The output signals from detector are in the form of voltages, these are measured from the detectors terminals. These signals are representative of the light incident on the detectors surface. The output signals are small, they are proportional to the amount of current flowing through the diode as a result light being detected. These signals are too small and are in the wrong format to be accurately detected by the microprocessor 3, so they are modified by output circuitry 6. This output circuitry 6 is comprised of two sections, namely an amplification section 7 and a conversion section 8. The amplification section 7 is comprised of an operational amplifier circuit. The gain provided by this circuit is dependant on the components used, therefore gain may be increased or decreased accordingly. Alternately other types of amplification circuit 7 may be used in a similar manner. Once the signal is amplified, it is converted from an analogue signal to a digital signal. This is performed either by a dedicated analogue-to-digital converter circuit 8 or in a analogue-to-digital converter contained within the microprocessor 3. The output signals from the detector are now in a format that the microprocessor 3 can identify and use.

Signals from the detector are continuously supplied to the microprocessor 3 as it is continuously measuring light incident on its surface. The microprocessor 3 takes discrete measurements from the continuously supplied signal and stores these signals in its memory.

The output of the detector reflects the presence of material in a sample. Once the test is completed, the microprocessor 3 stores the measured values in an array in its memory.

Data Analysis

Subsequent evaluation of these measured values may be made by a number of methods. Some trials and experimentation may be relied upon to determine the best method for obtaining values indicative of material presence in a sample. However, for ease of use, most embodiments will rely upon the comparison of received measured values with collected or stored data. This data may be values which have been pre-programmed into the microprocessor 3 so that the subsequent collection of initial set-up data by the user may not be required. This stored data may comprise of values typical for the type of samples to be analysed although it is envisaged for most embodiments that there will be provided provision for routine calibration using reference samples either to check accuracy and/or adjust the apparatus. Calibration information will be stored in the microprocessor 3 or in software being run by the external processing means. The use of software may be more flexible allowing for the updating of software to change the performance of the apparatus. In addition, calibration data is updated whenever a new calibration is run.

After treatment of all calibration data with a multiple regression method, the correlation factor and the intercept or the free factor are obtained. Summation of this formula results in typically eight locations in the total calibration data array. These eight readings relate to the locations that provided the best measurements.

The spectral response, material size and density is obtained by the multiplication of each individual sample reading at the predetermined position in the array with its regression coefficient factor and addition of the free factor as shown in the following formula:

$$\text{Result} = \text{free factor} + \sum_{n=1}^{8} coef_n \cdot meas_n$$

The invention claimed is:

1. An analyzer or spectrophotometer for the detection of material in a sample comprising:
    a source of radiation adapted to direct said radiation at least at said sample, the radiation incident on or affected by said sample able to be varied by varying the intensity of the said source radiation;
    a detector for detecting at least radiation affected by said sample, said detector having a spectral response able to be varied by biasing the detector and an output depending on radiation incident thereon and said spectral response;
    a controller or processor receiving said output, configured or programmed to:
    vary the spectral response of said detector using biasing to produce a sweep of detector spectral responses, each spectral response having a cut off wavelength dependent on the intensity of incident radiation and biasing;
    for each detector spectral response within the sweep of spectral responses, vary the intensity of said source radiation to produce a sweep of source radiation with a range of intensities directed at said sample;
    for each detector spectral response within the sweep of spectral responses, obtaining output from the detector resulting from the detection of each of the source radiation intensities affected by the sample, the detector output for each intensity being influenced by the detector's cut off wavelength at that intensity for that spectral response, wherein the combination of the detector's outputs at each of the intensities for the sweep of source radiation for each of the spectral responses in the detector sweep provide a combined set of data across a spectrum; and
    determine a characteristic of said sample based on said combined set of data.

2. A method of detecting material in a sample by using radiation directed at a sample and a detector to detect source radiation affected by the sample, the method comprising the steps of;
    varying the spectral response of said detector using biasing to produce a sweep of detector spectral responses, each spectral response having a cut off wavelength dependent on the intensity of incident radiation;
    directing radiation at said sample,
    for each detector spectral response within the sweep of spectral responses, varying the intensity of said radiation incident on or affected by said sample to produce a sweep of source radiation intensities,
    detecting at least radiation affected by said sample using the detector,
    for each detector spectral response within the sweep of spectral responses, obtain output from the detector resulting from the detection of each of the radiation intensities affected by said sample, the detector output for each intensity being influenced by the detector's cut off wavelength at that intensity for that spectral response, wherein the combination of the detector's outputs at each of the intensities for the sweep of radiation for each of the spectral responses in the detector sweep provide a combined set of data across a spectrum, and determining a characteristic of said sample based on said combined set of data.

3. An analyzer or spectrophotometer as claimed in claim 1 wherein the intensity of said source radiation directed at said sample is varied by varying the voltage or current supplied to the radiation source.

4. An analyzer or spectrophotometer as claimed in claim 1 wherein the intensity of said source radiation directed at said sample is varied by varying the transmission path between the radiation source and said sample.

5. An analyzer or spectrophotometer as claimed in claim 1 wherein the radiation affected by said sample is detected by a photodiode and the spectral response of said output is varied by varying the width of the depletion zone within said diode.

6. An analyzer or spectrophotometer as claimed in claim 5 wherein the width of the depletion zone within said diode is varied by varying the reverse voltage applied across the diode and the output being the resulting current.

7. An analyzer or spectrophotometer as claimed in claim 5 wherein said output signal from said detector is amplified and digitized prior to being supplied to said controller.

8. An analyzer or spectrophotometer as claimed in claim 7 wherein said controller is a microprocessor.

9. An analyzer or spectrophotometer as claimed in claim 7 wherein said detector is a photodiode detector.

10. An analyzer or spectrophotometer as claimed in claim 7 wherein said source is a light emitting diode.

11. An analyzer or spectrophotometer as claimed in claim 7 wherein said source is a tungsten filament lamp.

12. An analyzer or spectrophotometer as claimed in claim 7 wherein said source is a gas discharge lamp.

13. An analyzer or spectrophotometer for the detection of material in a sample according to claim 1 further comprising:
a variable transmission path for directing radiation in a first configuration between said source and said sample or in a second configuration between said source and said detector and
wherein, the controller or processor is further configured or programmed to:
control said variable transmission path between first and second configurations,
determine the radiation affected by said sample using said output of said detector,
determine the radiation directly from said source using said output of said detector, and
determine a characteristic of said sample based on said output of said detector in relation to variations in said transmission path.

14. An analyzer or spectrophotometer as claimed in claim 13 wherein when said variable transmission path is in the first configuration, radiation passes to said sampling along a sample path and when the variable transmission path is in the second configuration radiation passes directly to said detector along a reference path.

15. An analyzer or spectrophotometer as claimed in claim 14 wherein said variable transmission path is controlled between said first and second configurations using a blocking member having at least 3 cyclic modes comprising:
a first mode during which said blocking member is operated to control the variable transmission path into said second configuration where said radiation passes along said reference path,
a second mode during which said blocking member is operated to control said variable transmission path into said first configuration where said radiation passes along said sample path, and
a third mode during which said radiation is blocked.

16. An analyzer or spectrophotometer as claimed in claim 15 wherein said blocking member is rotatable about a central axis.

17. An analyzer or spectrophotometer as claimed in claim 16 wherein during said first mode the intensity of said radiation through said sample path is varied.

18. An analyzer or spectrophotometer as claimed in claim 17 wherein the intensity is varied by providing different sized apertures in an annular path through said blocking member.

19. An analyzer or spectrophotometer as claimed in claim 18 wherein said blocking member includes indexing and a sensor(s) to detect the position of said blocking member.

20. An analyzer or spectrophotometer as claimed in claim 1 wherein the intensity of the source radiation is varied by switching the source on, the transition from the off state to the on state resulting in a range of source radiation intensities that produces source radiation.

21. A method as claimed in claim 2 wherein the intensity of the source radiation is varied by switching the source on, the transition from the off state to the on state resulting in a range of source radiation intensities.

22. A method as claimed in claim 2 wherein the intensity of the source radiation directed at said sample is varied by varying the voltage or current supplied to the radiation source.

23. A method as claimed in claim 2 wherein the intensity of said source radiation directed at said sample is varied by varying the transmission path between the radiation source and said sample.

24. A method as claimed in claim 2 wherein the radiation affected by said sample is detected by a photodiode and the spectral response of said detector is varied by varying the width of the depletion zone within said diode.

25. A method as claimed in claim 24 wherein the width of the depletion zone within said diode is varied by varying the reverse voltage applied across the diode and the output being the resulting current.

26. A method as claimed in claim 2 wherein said output from said detector is amplified and digitized prior to being supplied to said controller.

27. A method according to claim 2 wherein the radiation transmission path is varied to direct radiation between said source and said sample in the first configuration or between said source and said detector in the second configuration, wherein the controller or processor is further configured or programmed to:
control a variable transmission path in said first configuration,
control a variable transmission path in said second configuration,
determine the output of the said detector in said first configuration,
determine the output of the said detector in said second configuration, and
determine a characteristic of said sample based on the difference of said outputs of said detector.

28. A method as claimed in claim 27 wherein when said variable transmission path is in the first configuration, radiation passes to said sample along a sample path and when the variable transmission path is in the second configuration, radiation passes directly to said detector along a reference path.

29. A method as claimed in claim 28 wherein said variable transmission path is controlled between said first and second configurations by controlling a blocking member into one of at least 3 cyclic modes comprising:

a first mode during which said blocking member is operated to control said variable transmission path into said first configuration where said radiation passes along said sample path, a second mode during which said blocking member is operated to control the variable transmission path into said second configuration where said radiation passes along said reference path, and a third mode during which said radiation is blocked.

30. A method as claimed in claim 29 wherein said blocking member is controlled into one of the modes by rotating the blocking member about a central axis.

31. A method as claimed in claim 30 further comprising varying the intensity of said radiation through said sample path during the first mode.

32. A method as claimed in claim 31 comprising varying the intensity by providing different sized apertures in an annular path through said blocking member.

33. An analyzer or spectrophotometer as claimed in claim 1 wherein:

as the intensity of source radiation increases for a particular spectral response of the detector, the intensity of the affected radiation increases resulting in the detection of a decreased range of wavelengths by the detector, and as the intensity of the source radiation decreases for a particular spectral response of the detector, the intensity of the affected radiation decreases resulting in the detection of an increased range of wavelengths by the detector, such that the combined set of data, being a combination of outputs from the detector at different intensities and spectral responses, provides information based on incident radiation detected at a range of different bandwidths by the detector.

* * * * *